US008759255B2

(12) United States Patent
Wacker

(10) Patent No.: US 8,759,255 B2
(45) Date of Patent: Jun. 24, 2014

(54) PESTICIDE PREPARATIONS

(75) Inventor: Andreas Wacker, Mannheim (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

(21) Appl. No.: 13/394,712

(22) PCT Filed: Sep. 4, 2010

(86) PCT No.: PCT/EP2010/005444
§ 371 (c)(1),
(2), (4) Date: Mar. 13, 2012

(87) PCT Pub. No.: WO2011/029561
PCT Pub. Date: Mar. 17, 2011

(65) Prior Publication Data
US 2012/0172223 A1    Jul. 5, 2012

(30) Foreign Application Priority Data
Sep. 10, 2009    (DE) .................. 10 2009 041 003

(51) Int. Cl.
*A01N 57/18*    (2006.01)
*A01N 25/00*    (2006.01)

(52) U.S. Cl.
USPC ................. 504/206; 504/360; 514/772.3

(58) Field of Classification Search
None
See application file for complete search history.

(56) References Cited

U.S. PATENT DOCUMENTS

| | | | |
|---|---|---|---|
| 4,853,026 A | 8/1989 | Frisch et al. | |
| 5,750,468 A | 5/1998 | Wright et al. | |
| 5,858,921 A | 1/1999 | Magin et al. | |
| 6,500,784 B1 | 12/2002 | Mille et al. | |
| 6,645,912 B1 | 11/2003 | Mille et al. | |
| 7,316,990 B2 * | 1/2008 | Tank et al. | 504/206 |
| 7,407,667 B2 | 8/2008 | Zerrer et al. | |
| 2005/0037926 A1 * | 2/2005 | Zerrer et al. | 504/324 |
| 2005/0130842 A1 * | 6/2005 | Fleute-Schlachter et al. | 504/206 |

FOREIGN PATENT DOCUMENTS

| | | |
|---|---|---|
| EP | 0 161 595 | 11/1985 |
| EP | 0 290 416 | 11/1988 |
| EP | 0 379 852 | 8/1990 |
| EP | 0 577 914 | 1/1994 |
| EP | 1 379 129 | 11/2002 |
| GB | 0 903 766 | 8/1962 |
| WO | WO 97/36491 | 10/1997 |
| WO | WO 98/06259 | 2/1998 |
| WO | WO 99/05914 | 2/1999 |
| WO | WO 00/38523 | 7/2000 |
| WO | WO 01/08481 | 2/2001 |
| WO | WO 01/08482 | 2/2001 |
| WO | WO 02/089575 | 11/2002 |
| WO | WO 03/063589 | 8/2003 |

OTHER PUBLICATIONS

International Search Report for PCT/EP2010/005444, dated Apr. 11, 2011.
Translation of the Internatonal Preliminary Report on Patentability for PCT/EP2010/005444, dated Apr. 11, 2011.
English Abstract for EP 0161595, Nov. 21, 1985.
English Abstract for JP publication No. 61108781, May 27, 1986.
English Abstract for CS 245183, Aug. 14, 1986.
English Abstract for JP publication No. 62243888, Oct. 24, 1987.
English Abstract for JP publication No. 03-097789, Apr. 23, 1991.
English Abstract for JP publication No. 06-166602, Jun. 14, 1994.
English Abstract for JP publication No. 11-209231, Aug. 3, 1999.
English Abstract for WO 01/08481, Feb. 8, 2001.
English Abstract for DE19936092, Feb. 1, 2001.

* cited by examiner

*Primary Examiner* — Tracy Vivlemore
*Assistant Examiner* — Monica Shin
(74) *Attorney, Agent, or Firm* — Tod A. Waldrop

(57) ABSTRACT

The invention relates to compositions containing a) one or more pesticides, b) one or more copolymers obtained by the copolymerization of i) glycerol, ii) at least one dicarboxylic acid, and iii) at least one monocarboxylic acid, c) one or more amphoteric surface-active substances, and d) water. The compositions are particularly suitable for controlling and/or combating weeds, fungal diseases, or insect infestation.

12 Claims, No Drawings

# PESTICIDE PREPARATIONS

The invention relates to aqueous, storage-stable pesticide preparations which comprise mixtures of copolymers and amphoteric surfactants.

Pesticides (acaricides, bactericides, fungicides, herbicides, insecticides, molluscicides, nematicides, and rodenticides) are chemical or natural substances which penetrate into plant cells, plant tissue or parasitic organisms in or on the plant and cause them damage and/or destruction.

The largest proportion of pesticides is represented by herbicides, followed by insecticides and fungicides.

The most important herbicides are chemical substances which act on the transport system of plants, by means, for example, of inhibition of photosynthesis, fatty acid biosynthesis or amino acid biosynthesis, and lead to the inhibition of germination and growth through to the dying of the plant.

Known herbicides are, for example, herbicides from the N-phosphono-methyl-glycine substance class (glyphosates). Glyphosates are used in large amounts in the agricultural economy, as highly eco-friendly herbicides which are at the same time highly effective and widely deployable. They are applied preferably in the form of water-soluble salts, as for example in the form of alkali metal, ammonium, monoalkyl- or dialkylammonium, mono-, di- or triethanolammonium, alkylsulfonium or alkyphosphonium salt, and also in the form of mixtures of these salts, as aqueous formulations, but also in solid form, to leaves and grasses, where they act on the transport system of the plant and destroy it.

The biological activity of a pesticide can be determined from the plant growth or damage to the plants as a result of exposure to the active ingredient on the leaf or via the roots, as a function of the activity time and the active concentration.

A general problem is that only a fraction of the active ingredient develops the desired activity. By far the largest part is lost unused, with the active ingredient, during delivery of the spray liquor, failing to reach the leaves or roots of the plant and seeping unused in the soil, being washed off by rain, or not being taken up by the plant.

This ecological and economic disadvantage can be reduced by addition of auxiliaries (adjuvants) to pesticide formulations. These auxiliaries may, for example, reduce spray drift, improve the wetting of the plant, or ensure that the active ingredient adheres for a longer time on the plant surface or is taken up more effectively. With glyphosate formulations in particular, the nature and amount of the adjuvant used has a decisive influence on the activity of the formulation.

Widely used adjuvants in glyphosate formulations are fatty amine ethoxylates, principally tallow fatty amine ethoxylates and alkyl ether amine ethoxylates (EP 0 290 416, U.S. Pat. No. 5,750,468). These compounds, however, are classed as not unobjectionable, on account of their eco-toxicological properties, more particularly their effect on aquatic organisms.

EP 1 379 129 and WO 03/000055 describe pesticide preparations which comprise a copolymer of glycerol, a carboxylic acid, and a dicarboxylic acid as adjuvant. These copolymers significantly increase the effect of the pesticides and are notable for their low toxicity and high eco-friendliness.

A disadvantage associated with the use of these copolymers in aqueous pesticide preparations is the inadequate storage stability at relatively high temperatures, especially if the copolymers are present in the preparation only in a relatively small amount.

Considered a further disadvantage associated with the use of these copolymers is the high viscosity of the pesticide preparations, especially when they are highly loaded formulations containing a high level of active substance. The use of amphoteric surfactants such as alkylbetaines, alkyl(amidoalkyl)-betaines or amine oxides as adjuvants in pesticide preparations such as, for example, in glyphosate formulations is known.

WO 97/36491 describes the use of amine oxides as adjuvants in glyphosate formulations.

WO 00/38523 describes the use of amphoteric surfactants in combination with ether carboxylates as adjuvants in glyphosate formulations, the amphoteric surfactants being betaines having a particularly low sodium chloride content, which are complicated and, accordingly, expensive to produce.

A similar composition is described in WO 01/08482, with alkylamidoamine oxides being used as amphoteric surfactant in combination with ether carboxylates as adjuvants in glyphosate formulations.

WO 03/063589 describes the use of alkylbetaines or alkyl (amidoalkyl)-betaines in combination with various other additives such as fatty amine ethoxylates in glyphosate formulations.

A disadvantage of these adjuvants is that on account of their production process they are available only as dilute aqueous solutions, containing typically 30%-35% by weight of active substance. Moreover, these solutions (as in the case of the alkylbetaines) may comprise considerable amounts of salts such as sodium chloride, obtained as a byproduct during production, and this usually impacts adversely on the stability of the pesticide formulation.

The low active content of the amphoteric surfactant solutions, moreover, has the disadvantage that large quantities of water have to be transported, which is uneconomic.

Particularly in the case of highly concentrated pesticide preparations, such as glyphosate formulations, the low active content of amphoteric surfactant in conjunction with the high water fraction also means that it is not possible to add a sufficiently large amount of adjuvant to the formulation.

Glyphosate formulations are typically prepared from highly concentrated aqueous solutions of glyphosate salts, which inevitably contain significant amounts of water. The formulation is produced by mixing with the adjuvant and optionally further auxiliaries. The greater the amount of water introduced additionally into the formulation during this procedure, the less the amount of adjuvant and other auxiliaries that the formulation can ultimately comprise. With the amphoteric surfactants it may be the case that, in order to allow the desired glyphosate concentration to be maintained, it is possible to add only a suboptimum amount of adjuvant, and this reduces the efficacy of the formulation. Furthermore, the amphoteric surfactants are not toxicologically unobjectionable, since they are classed as strongly irritant to the eyes.

The problem which presented itself was that of developing new, highly active aqueous pesticide preparations which can be made available also in the form of storage-stable, low-viscosity, aqueous formulations and which are advantageous from the standpoints of toxicology, ecology, and economics.

The problem is solved, surprisingly, by the aqueous pesticide preparation comprising not only the one or two or more pesticides but also a mixture which is composed of one or more copolymers obtainable by copolymerizing glycerol, at least one dicarboxylic acid, and at least one monocarboxylic acid, and also one or more amphoteric surface-active substances.

Through the use of this mixture it is possible to prepare storage-stable pesticide preparations which are distinguished by a low viscosity, even at low temperature.

The invention provides compositions comprising
a) one or more pesticides,
b) one or more copolymers obtainable by copolymerizing
   i) glycerol,
   ii) at least one dicarboxylic acid, and
   iii) at least one monocarboxylic acid,
c) one or more amphoteric surface-active substances, and
d) water.

The mixtures of the compounds selected from components b) and c) are referred to below as adjuvant mixtures.

The adjuvant mixtures comprising the components b) and c) are suitable as an adjuvant in the pesticide preparations of the invention for improving the biological activity of herbicides, insecticides, fungicides, acaricides, bactericides, molluscicides, nematicides, and rodenticides, preferably of herbicides.

Suitable herbicides are—without the invention being confined to these—amide herbicides such as saflufenacil, anilide herbicides such as propanil, chloroacetanilide herbicides such as acetochlor, alachlor, butachlor, metolachlor, sulfonanilide herbicides such as florasulam, metosulam, sulfonamide herbicides such as carbasulam, penoxsulam, pyroxsulam, benzoic acid herbicides such as dicamba, tricamba, picolinic acid herbicides such as aminopyralid, picloram, benzoylcyclohexanedione herbicides such as mesotrione, tembotrione, benzofuranyl alkylsulfonate herbicides such as ethofumesate, benzothiazole herbicides such as benzthiazuron, carbamate herbicides such as asulam, chlorprocarb, fenasulam, carbanilate herbicides such as carbasulam, carbetamide, desmedipham, phenmedipham, cyclohexene oxime herbicides, such as butroxydim, dicarboximide herbicides such as flumezin, dinitroaniline herbicides such as pendimethalin, trifluralin, dinitrophenol herbicides, such as etinofen, nitrophenyl ether herbicides such as etnipromid, nitrofen, imidazolinone herbicides such as imazapyr, imazethapyr, nitrile herbicides such as bromoxynil, pyraclonil, organophosphorus herbicides as anilofos, glufosinate, glyphosate, oxadiazolone herbicides such as dimefuron, oxazole herbicides such as topramezone, phenoxy herbicides such as etnipromid, phenoxyacetic herbicides such as MCPA, MCPA-thioethyl, phenoxybutyric acid herbicides such as MCPB, phenoxypropionic acid herbicides such as dichlorprop, fenoprop, aryloxyphenoxypropionic acid herbicides such as clodinafop, fenoxaprop, quizalofop, phenylenediamine herbicides such as prodiamine, pyrazole herbicides such as difenzoquat, metazachlor, pyrazosulfuron, benzoylpyrazole herbicides such as topramezone, phenylpyrazole herbicides such as pinoxaden, pyraflufen, pyridazinone herbicides such as oxapyrazon, pyridine herbicides such as aminopyralid, diflufenican, fluoroxypyr, picloram, pyroxsulam, quaternary ammonium herbicides such as diquat, paraquat, thiocarbamate herbicides such as ethiolate, methiobencarb, thiobencarb, thiourea herbicides such as methiuron, indaziflam, chlorotriazine and methoxytriazine herbicides such as atrazine, simazine, simeton, terbumeton, methylthiotriazine herbicides such as prometryn, simetryn, triazinone herbicides such as hexazinone, triazole herbicides such as flupoxam, triazolone herbicides such as flucarbazone, thiencarbazone, triazolopyrimidine herbicides such as flumetsulam, metosulam, phenoxsulam, pyroxsulam, uracil herbicides such as butafenacil, saflufenacil, urea and phenylurea herbicides such as benzthiazuron, diuron, isoproturon, sulfonylurea herbicides such as amidosulfuron, bensulfuron, foramsulfuron, halosulfuron, mesosulfuron, nicosulfuron, oxasulfuron, pyrazosulfuron, rimsulfuron, sulfosulfuron, trifloxysulfuron, triazinylsulfonyl-urea herbicides such as chlorsulfuron, iodosulfuron, metsulfuron.

These may be individual active ingredients or combinations of two or more active ingredients. The pesticide preparations may take the form, for example, of aqueous solutions (SL formulations), aqueous suspensions (SC formulations), emulsions in water (EW formulations), microemulsions in water (ME formulations) or suspoemulsions in water (SE formulations). It is possible here for one or more active ingredients to be in solution or suspension in water, while one or more other active ingredients are present in a nonaqueous phase.

Preferred pesticides of component a) are selected from the N-phosphono-methyl-glycine substance class (glyphosate).

Among the glyphosates, the free acid and the water-soluble salts are preferred. With particular preference the pesticide or two or more pesticides of component a) are selected from water-soluble salts of N-phosphono-methyl glycine (glyphosate).

Among the water-soluble salts of glyphosate, preference is given in turn to the alkali metal, ammonium, monoalkyl- or dialkylammonium, mono-, di- or triethanolammonium, alkylsulfonium, alkylphosphonium, sulfonylamine or aminoguanidine salts and also mixtures of these salts. In this context, "monoalkylammonium" with particular preference means "isopropyl-ammonium". Among the alkali metal salts, the potassium salt is particularly preferred.

Preferred copolymers of component b) are obtainable by copolymerizing
i) glycerol,
ii) at least one dicarboxylic acid, and
iii) at least one monocarboxylic acid of formula (I)

$$R^1\text{—COOH} \tag{I}$$

where $R^1$ is $(C_5\text{-}C_{29})$-alkyl; $(C_7\text{-}C_{29})$-alkenyl; phenyl or naphthyl, and comprise 19.9% to 99% by weight of component i), 0.1% to 30% by weight of component ii), and 0.9% to 80% by weight of component iii).

Preferred dicarboxylic acids of component ii) are selected from aromatic dicarboxylic acids. Particularly preferred dicarboxylic acids of component ii) are selected from phthalic acid, terephthalic acid or isophthalic acid.

Preferred monocarboxylic acids of component iii) are selected from monocarboxylic acids of the formula (I) (formula $R^1$—COOH), in which $R^1$ is preferably an alkyl or alkenyl group and more preferably a linear alkyl or alkenyl group. With further preference $R^1$ in the monocarboxylic acids of the formula (I), where it is an alkyl or alkenyl group, possesses 8 to 22 carbon atoms. With particular preference the monocarboxylic acids of the formula (I) are those in which $R^1$ is a fatty alkyl radical having 8 to 22 carbon atoms. Exceptionally preferred are the monocarboxylic acids of the formula (I) selected from coconut fatty acid or tallow fatty acid.

The preparation of the copolymers of component b) is described in EP 1 379 129 and WO 03/000055, for example.

Preferred amphoteric surface-active substances of component c) are selected from the formulae (II) to (V)
iv) alkylbetaine of the formula (II)

$$R^1R^2R^3N^+\text{—}CH_2\text{—}COO^- \tag{II}$$

where $R^1$ is a linear or branched alkyl group having 3 to 30 carbon atoms or a mixture thereof, $R^2$ and $R^3$ may be identical or different and are hydrogen, an alkyl group having 1 to 10 carbon atoms or a group of the formula $(C_2H_4O)_pH$, and p is a number from 1 to 10, v) alkyl(amidoalkyl)-betaine of the formula (III)

$$R^1\text{—CONH—}(CH_2)_n N^+R^2R^3\text{—}CH_2\text{—}COO^- \tag{III}$$

where $R^1$ is a linear or branched alkyl group having 3 to 30 carbon atoms or a mixture thereof, $R^2$ and $R^3$ may be identical or different and are hydrogen, an alkyl group having 1 to 10 carbon atoms or a group of the formula $(C_2H_4O)_pH$, and n and p are numbers from 1 to 10, vi) amine oxide of the formula (IV)

$$R^1NR^2R^{3+}\!\!-\!\!O^- \qquad \qquad (IV)$$

where $R^1$ is a linear or branched alkyl group having 3 to 30 carbon atoms or a mixture thereof, $R^2$ and $R^3$ may be identical or different and are hydrogen, an alkyl group having 1 to 10 carbon atoms or a group of the formula $(C_2H_4O)_pH$, and p is a number from 1 to 10, vii) amine oxide of the formula (V)

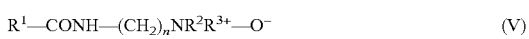

$$R^1\!\!-\!\!CONH\!\!-\!\!(CH_2)_nNR^2R^{3+}\!\!-\!\!O^- \qquad (V)$$

where $R^1$ is a linear or branched alkyl group having 3 to 30 carbon atoms or a mixture thereof, $R^2$ and $R^3$ may be identical or different and are hydrogen, an alkyl group having 1 to 10 carbon atoms or a group of the formula $(C_2H_4O)_pH$, and n and p are numbers from 1 to 10.

In the compounds of the formulae (II), (III), (IV), and (V) the radicals $R^1$ are preferably linear alkyl groups. With further preference $R^1$ in the compounds of the formulae (II), (III), (IV), and (V) possesses 8 to 22 carbon atoms.

In the compounds of the formulae (II), (III), (IV), and (V) $R^2$ and $R^3$ are preferably alkyl groups and more particularly alkyl groups having 1 to 4 carbon atoms. With particular preference $R^2$ and $R^3$ in the compounds of the formulae (II), (III), (IV), and (V) are methyl groups.

In the groups $(C_2H_4O)_pH$, p is preferably 1 to 3.

In the compounds of the formulae (III) and (V), n is preferably 3.

Preferred amphoteric surface-active substances of component c) are compounds of the formulae (II) and (V). Preferred among the compounds of the formula (II) are those in which $R^1$ is alkyl having 8 to 22 carbon atoms, preferably linear alkyl having 8 to 22 carbon atoms, and $R^2$ and $R^3$ are methyl. Preferred among the compounds of the formula (V) are those in which $R^1$ is alkyl having 8 to 22 carbon atoms, preferably linear alkyl having 8 to 22 carbon atoms, $R^2$ and $R^3$ are methyl, and n is 3.

The amphoteric surface-active substances of the formulae (II), (III), (IV), and (V) can be acquired commercially. Copolymers of component b) are likewise available commercially.

With the above-described adjuvant mixtures comprising the components b) and c) it is possible to prepare aqueous pesticide formulations, more particularly glyphosate formulations, having excellent storage stability. The storage stability is higher than for formulations containing only component b) as adjuvant. The irritant effect, and more particularly the irritant effect on the eyes, is reduced in comparison to formulations which contain merely component c) as adjuvant. Further performance advantages are the low viscosity and also the high solubility behavior in water.

One important criterion for the storage stability of glyphosate formulations is the phase stability. In this context, the cloud point, as it is known, is a parameter for determining the phase stability. The cloud point is the temperature to which an aqueous formulation can be heated without phase separation. Before the cloud point is reached, the surfactants and the glyphosate salt are present in defined concentrations in the aqueous formulation, as a clear, homogeneous solution. On heating to temperatures above the cloud point, the initially transparent formulation first becomes cloudy, the surfactant separates from the solution, and on standing there is phase separation.

The cloud point of a composition is customarily determined by heating the solution until clouding occurs. After that, the composition is cooled with stirring and with continual temperature checking. The temperature at which the clouded solution becomes clear again is recorded as the measured value of the cloud point.

It is known that the storage stability of glyphosate formulations can be improved by addition of glycols and polyglycols such as ethylene glycol, propylene glycol or polyethylene glycols. These compounds, however, do not act as adjuvants, and therefore limit the scope for the addition of an adjuvant. Furthermore, these compounds may have the unwanted effect of increasing the viscosity of the formulations.

The adjuvant mixture consisting of component b) and component c), furthermore, exhibits synergistic boosting of the effect of the pesticides. This means that, with the same amount of adjuvant, a combination of components b) and c) exhibits a greater effect than the same amount of pure adjuvant b) or c).

In one preferred embodiment of the invention the pesticide or two or more pesticides of component a) are selected from glyphosate, with the amount of glyphosate in the compositions of the invention being from 80 to 600 g/l, based on the glyphosate acid equivalent. These quantity figures relate to the composition of the invention as a whole. Preferred as glyphosate in this context are, again, water-soluble salts of glyphosate.

In another preferred embodiment of the invention, the sum of the amounts of components b) and c) in the compositions of the invention is from 20 to 250 g/l and preferably from 50 to 200 g/l. These quantity figures are based on the composition of the invention as a whole.

In another preferred embodiment of the invention, the weight ratio of the one or more compounds of component b) to the one or more compounds of component c) is from 95:5 to 5:95 and preferably from 80:20 to 20:80.

The amount of pesticides and the abovementioned adjuvant mixtures composed of components b) and c) in the pesticide preparations of the invention may vary within wide limits.

In a further preferred embodiment of the invention, the compositions take the form of concentrate formulations which are diluted prior to use, more particularly with water (for example, "ready-to-use", "in-can" or "built-in" formulations), and comprise the pesticide or two or more pesticides of component a) in amounts from 5% to 80% by weight, preferably from 20% to 60% by weight, and more preferably from 30% to 57% by weight, and the adjuvant mixture composed of components b) and c) in amounts from 1% to 50% by weight, preferably from 3% to 30% by weight, and more preferably from 5% to 20% by weight. These quantity figures are based on the concentrate formulation as a whole.

The concentrate formulations are phase-stable even under temperature exposure at 20 to 55° C., preferably at 5 to 70° C., and more preferably at 0 to 80° C.

The preparations are delivered to the fields in the form of spray liquors. The spray liquor in this case is prepared by diluting the concentrate formulation with a defined amount of water.

In a further preferred embodiment of the invention, the composition takes the form of a spray liquor and comprises 0.001% to 10% by weight, preferably 0.02% to 3% by weight, and more preferably 0.025% to 2% by weight of pesticide of component a) and 0.001% to 3% by weight, preferably 0.005% to 1% by weight, and more preferably 0.01% to 0.5% by weight of adjuvant mixture composed of components b) and c). The stated quantity figures are based on the spray liquor as a whole.

The weight ratio of adjuvant mixture composed of components b) and c) to pesticide of component a) in the spray liquor is preferably from 1:100 to 10:1, more preferably from 1:20 to 2:1 and with particular preference from 1:12 to 1:2.

A great performance advantage is the high salt stability of the preparations of the invention in the aqueous medium, even with high pesticide concentration and salt concentration, as manifested in the clear appearance of these formulations, with cloud points above 55° C.

The preparations of the invention may comprise thickeners, solvents, dispersants, emulsifiers, preservatives, other adjuvants, binders, diluents, disintegrants, wetting agents, low-temperature stabilizers, and defoamers.

As thickeners it is possible to use xanthan gum and/or cellulose, as for example carboxy-, methyl-, ethyl- or propylcellulose or (optionally modified) bentonites in the amounts by weight of 0.01% to 5%, based on the completed composition. Examples of suitable solvents include N-methyl-pyrrolidone, butyrolactone, lactic esters such as ethylhexyl lactate, esters of carbonic acid such as propylene carbonate, fatty acid amides such as N,N-dimethyldecanamide, esters of phosphorous acid or of phosphoric acid such as tris(ethylhexyl) phosphate, glycols, polyethylene glycols, propylene glycol, and animal and mineral oils. Suitable dispersants and emulsifiers are nonionic, amphoteric, cationic, and anionic surfactants. As preservatives it is possible to use organic acids and their esters, as for example ascorbic acid, ascorbyl palmitate, sorbate, benzoic acid, methyl and propyl 4-hydroxybenzoate, propionates, phenol, as for example 2-phenylphenate, 1,2-benzisothiazolin-3-one, formaldehyde, sulfurous acid, and the salts thereof. Further adjuvants may be polyglycerol esters, alcohol alkoxylates such as, for example, alcohol ethoxylates, alkylpolysaccharides, fatty amine ethoxylates, sorbitan and sorbitol ethoxylate derivatives, and derivatives of alk(en)ylsuccinic acid.

Binders contemplated for solid formulations include polyvinylpyrrolidone, polyvinyl alcohol, carboxymethylcellulose, sugars, as for example sucrose, sorbitol or starch. Suitable diluents, absorbers or carriers include carbon black, tallow, kaolin, aluminum, calcium or magnesium stearate, sodium tripolyphosphate, sodium tetraborate, sodium sulfate, silicates, and sodium benzoate. Acting as disintegrants are cellulose, as for example carboxymethylcellulose, polyvinylpyrrolidone, sodium or potassium acetate, carbonates, bicarbonates, sesquicarbonates, ammonium sulfate or potassium hydrogenphosphate.

As wetting agents it is possible to use alcohol ethoxylates/propoxylates. Functioning as low-temperature stabilizers may be all customary substances which can be used for that purpose. Examples include urea, glycerol, and propylene glycol. Suitable defoamers are fatty acid alkyl ester alkoxylates; organopolysiloxanes such as polydimethylsiloxanes and mixtures thereof with microfine, optionally silanized silica; perfluoroalkylphosphonates and -phosphinates; paraffins; waxes and microcrystalline waxes and mixtures thereof with silanized silica. Also advantageous are mixtures of different foam inhibitors, examples being those comprising silicone oil, liquid paraffin and/or waxes.

The compositions of the invention may further comprise one or more agrochemical salts, preferably ammonium salts or potassium salts, as for example potassium nitrate, potassium phosphate, potassium hydrogenphosphate, potassium dihydrogenphosphate or potassium lactate. The compositions of the invention can be applied by the customary methods. Aqueous concentrates and solid formulations are diluted with the appropriate amount of water prior to being applied.

Pesticide quantities per hectare of typically in the range from 0.05 to 5 kg are delivered. The fraction of the adjuvant mixture consisting of the compounds selected from components b) and c) is in the range from preferably 0.002 to about 1.0 kg/ha. The volume for the pesticide formulation produced for spray delivery is preferably in the range from 50 to 1000 l/ha.

The invention further relates to the use of a composition of the invention for the checking and/or control of weeds, fungal diseases or insect infestation. The use of the preparation for the checking and/or control of weeds is preferred.

These uses may preferably also take place in what is called the tank-mix method. In these cases, therefore, the pesticide or pesticides and the adjuvant mixture consisting of one or more compounds of component b) and one or more compounds of component c), and also the water, may also be present in the form of what is called a "tank-mix" preparation. In such a preparation, the pesticide or pesticides and the adjuvant mixture are present separately from one another. The two preparations are mixed with one another prior to delivery, generally a short time before, to produce a preparation of the invention.

In the tank-mix method, the pesticide is present, before mixing, as a formulation in water and/or in an organic solvent, or as a solid formulation.

In the tank-mix method, the adjuvant mixture prior to mixing is preferably in solution in water or in a solvent mixture of water and polyethylene glycol, propylene glycol or glycerol.

EXAMPLES

The invention is illustrated below by examples which should, however, in no way be considered to impose any restriction.

Example 1

Various pesticide preparations (see Table 1) are adjusted to a concentration of 360 g/l a.e. (a.e.: acid equivalent of glyphosate) by mixing a commercial aqueous solution of glyphosate-isopropylammonium (with 62% by weight active ingredient) with components b) and c) and also water and optionally propylene glycol.

The cloud point and the viscosity of the glyphosate formulations prepared in this way are ascertained.

TABLE 1

Glyphosate formulations

| Formulation | 1 (comparative) | 2 (comparative) | 3 (invention) |
|---|---|---|---|
| Glyphosate IPA salt [g] (62% by weight) | 78.4 | 78.4 | 78.4 |
| Component b) [g] | 9.0 | 9.0 | 7.9 |
| Component c) [g] | — | — | 2.4 |
| Propylene glycol [g] | — | 3.0 | — |
| Water [g] | 28.5 | 25.5 | 27.2 |
| Cloud point [° C.] | 56 | 78 | >90 |
| Viscosity at 5° C. [mPa · s] | 40 | 60 | 35 |

Component b) = Synergen ® GL 5 (copolymer consisting of glycerol, coconut fatty acid, and phthalic acid; product from Clariant), 70% strength by weight solution in water.
Component c) = cocoamido-N-[3-(dimethylamino)propyl], N-oxide, 30% strength by weight solution in water.

Formulation 1 contains only component b) as adjuvant. The formulation has a cloud point of only 56° C.; a formulation of this kind does not possess sufficient storage stability.

Formulation 2, in addition to component b), contains propylene glycol, in order to stabilize the formulation and to raise the cloud point. This is accomplished to a certain extent (rise in cloud point from 56° C. to 78° C.), but at the same time the viscosity increases from 40 mPa·s to 60 mPa·s.

In the inventive formulation 3, some of component b) has been replaced by component c). The total adjuvant amount (based on the active content) remains the same. The stability of the formulation increases markedly (the cloud point rises from 56° C. to >90° C.), and additionally there is a reduction in viscosity from 40 to 35 mPa·s.

The invention claimed is:

1. A composition comprising:
   a) at least one pesticide,
   b) at least one copolymer prepared by copolymerizing
      i) glycerol,
      ii) at least one dicarboxylic acid, and
      iii) at least one monocarboxylic acid,
   c) at least one amphoteric surface-active substance, and
   d) water, wherein the at least one pesticide of component a) is selected from the group consisting of N-phosphonomethyl-glycine (glyphosate) substance class.

2. A composition as claimed in claim 1, wherein the at least one pesticide of component a) is selected from the group consisting of water-soluble salts of N-phosphonomethyl-glycine (glyphosate).

3. A composition as claimed in claim 1, wherein the at least one copolymer of component b) is selected from the group consisting of copolymers prepared by copolymerizing
   i) glycerol,
   ii) at least one dicarboxylic acid, and
   iii) at least one monocarboxylic acid of formula (I)

$R^1$—COOH    (I), where $R^1$ is ($C_5$-$C_{29}$)-alkyl; ($C_7$-$C_{29}$)-alkenyl; phenyl or naphthyl, and comprise 19.9% to 99% by weight of component i), 0.1% to 30% by weight of component ii), and 0.9% to 80% by weight of component iii).

4. A composition as claimed in claim 1, wherein the at least one amphoteric surface-active substance of component c) is selected from the group consisting of formulae (II) to (V)

iv) alkylbetaine of the formula (II)

$R^1R^2R^3N^+$—$CH_2$—$COO^-$    (II)

where $R^1$ is a linear or branched alkyl group having 3 to 30 carbon atoms or a mixture thereof, $R^2$ and $R^3$ may be identical or different and are hydrogen, an alkyl group having 1 to 10 carbon atoms or a group of the formula $(C_2H_4O)_pH$, and p is a number from 1 to 10, v) alkyl(amidoalkyl)-betaine of the formula (III)

   $R^1$—CONH—$(CH_2)_n$$N^+R^2R^3$—$CH_2$—$COO^-$    (III)

where $R^1$ is a linear or branched alkyl group having 3 to 30 carbon atoms or a mixture thereof, $R^2$ and $R^3$ may be identical or different and are hydrogen, an alkyl group having 1 to 10 carbon atoms or a group of the formula $(C_2H_4O)_pH$, and n and p are numbers from 1 to 10, vi) amine oxide of the formula (IV)

   $R^1NR^2R^{3+}$—$O^-$    (IV)

where $R^1$ is a linear or branched alkyl group having 3 to 30 carbon atoms or a mixture thereof, $R^2$ and $R^3$ may be identical or different and are hydrogen, an alkyl group having 1 to 10 carbon atoms or a group of the formula $(C_2H_4O)_pH$, and p is a number from 1 to 10, and vii) amine oxide of the formula (V)

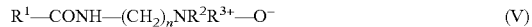
   $R^1$—CONH—$(CH_2)_n$$NR^2R^{3+}$—$O^-$    (V)

where $R^1$ is a linear or branched alkyl group having 3 to 30 carbon atoms or a mixture thereof, $R^2$ and $R^3$ may be identical or different and are hydrogen, an alkyl group having 1 to 10 carbon atoms or a group of the formula $(C_2H_4O)_pH$, and n and p are numbers from 1 to 10.

5. A composition as claimed in claim 1, wherein the at least one pesticide of component a) is selected from the group consisting of glyphosate, and water-soluble salts of glyphosate, and the amount of glyphosate in the composition is from 80 to 600 g/l, based on the glyphosate acid equivalent.

6. A composition as claimed in claim 1, wherein the sum of the amounts of components b) and c) is from 20 to 250 g/l.

7. A composition as claimed in claim 1, wherein the weight ratio of the at least one compound of component b) to the at least one compound of component c) is from 95:5 to 5:95.

8. A composition as claimed in claim 1, which is present in the form of a concentrate formulation which is diluted prior to use, and comprises 5% to 80% by weight, of pesticide of component a) and a total amount of compounds selected from components b) and c) of 1% to 50% by weight.

9. A composition as claimed in claim 1, which is present in the form of a spray liquor, and comprises 0.001% to 10% by weight, of pesticide of component a) and a total amount of compounds selected from components b) and c) of 0.001% to 3% by weight.

10. A composition as claimed in claim 1, which comprises at least one agrochemical salt selected from the group consisting of ammonium salts and potassium salts.

11. A process for the checking and/or control of weeds, fungal diseases or insect infestation comprising the step of contacting the weeds, fungal diseases or insect infestation with a composition as claimed in claim 1.

12. A process as claimed in claim 11, wherein the process includes a step comprising a tank-mix preparation.

* * * * *